United States Patent [19]

Rao

[11] Patent Number: 5,824,828
[45] Date of Patent: Oct. 20, 1998

[54] PROCESS FOR MANUFACTURE OF TRICHLOROTRIFLUOROETHANES

[75] Inventor: Velliyur Nott Mallikarjuna Rao, Wilmington, Del.

[73] Assignee: E. I. du Pont de Nemours and Company, Wilmington, Del.

[21] Appl. No.: 637,631

[22] PCT Filed: Sep. 1, 1994

[86] PCT No.: PCT/US94/09532

§ 371 Date: Apr. 29, 1996

§ 102(e) Date: Apr. 29, 1996

[87] PCT Pub. No.: WO95/12565

PCT Pub. Date: May 11, 1995

[51] Int. Cl.[6] .................................................. C07C 17/00
[52] U.S. Cl. .......................................... 570/168; 570/151
[58] Field of Search ............................................. 570/168

[56] References Cited

U.S. PATENT DOCUMENTS

| | | | |
|---|---|---|---|
| 2,598,411 | 5/1952 | Miller et al. | 260/653 |
| 3,632,834 | 1/1972 | Christoph | 260/653.7 |
| 4,925,993 | 5/1990 | Zawalski | 570/151 |
| 5,017,732 | 5/1991 | Zawalski | 570/151 |
| 5,136,113 | 8/1992 | Rao | 570/176 |

FOREIGN PATENT DOCUMENTS

| | | | |
|---|---|---|---|
| 0 317 981 | 5/1989 | European Pat. Off. | C07C 19/08 |
| 0 404 297 | 12/1990 | European Pat. Off. | C07C 17/24 |
| 1 903 556 | 7/1969 | Germany . | |

OTHER PUBLICATIONS

Gervasutti, C. et al., J. Fluorine Chem., 19, 1–20, 1981/82.

Bitner, J.L. et al., U.S. Dept. Comm. Off. Tech. Serv. Rep. 136732, 25–27, 1958.

*Primary Examiner*—Paul J. Killos

[57] ABSTRACT

This invention relates to a process for the manufacture of $C_2Cl_3F_3$ reaction product from a mixture of $C_2Cl_4F_2$ isomers, and more particularly to the manufacture of $C_2Cl_3F_3$ reaction product which is substantially free of $CClF_2CClF_2$.

10 Claims, 1 Drawing Sheet

PROCESS FOR MANUFACTURE OF TRICHLOROTRIFLUOROETHANES

BACKGROUND

Tetrachlorodifluoroethanes are readily converted to trichlorotrifluoroethanes ($C_2Cl_3F_3$) by using conventional fluorination. The $C_2Cl_3F_3$ product typically contains greater than 98% of the more symmetrical isomer, $CCl_2FCClF_2$ (CFC-113). CFC-113 can be readily isomerized to its more unsymmetrical isomer, $CCl_3CF_3$ (CFC-113a) using aluminum trihalide catalyst. CFC-113a can in turn be converted to 1,1-dichlorotetrafluoroethane (i.e., $CCl_2FCF_3$ or CFC-114a) by conventional fluorination. $CCl_2FCF_3$ is of interest as an intermediate to 1,1,1,2-tetrafluoroethane (i.e., $CF_3CH_2F$ or HFC-134a) which can be obtained via catalytic hydrogenolysis of its carbon-chlorine bonds using a supported metal hydrogenation catalyst (see e.g., C. Gervasutti et al., J. Fluorine Chem., 1981/82, 19, pgs. 1–20). HFC-134a is an environmentally acceptable potential replacement for chlorofluorocarbon (i.e., CFC) refrigerants, blowing agents, aerosol propellants and sterilants that are being viewed with concern in connection with the destruction of stratospheric ozone. It is highly desired that the 1,1-dichlorotetrafluoroethane employed in the hydrogenolysis route to HFC-134a has as low a content of 1,2-dichlorotetrafluoroethane (i.e., $CClF_2CClF_2$ or CFC-114) as practicable since the presence of CFC-114 during hydrogenolysis can lead to formation of 1,1,2,2-tetrafluoroethane (i.e., $CHF_2CHF_2$ or HFC-134; see e.g., J. L. Bitner et al., U.S. Dep. Comm. Off. Tech. Serv. Rep. 136732, (1958), p. 25). HFC-134 mixed in HFC-134a may be objectionable for some applications depending on concentration and, since the two isomers boil only 7° C. apart, separation of the isomers in high purity is difficult.

There remains a need for processes which facilitate the production of CFC-114a substantially free of its isomer, particularly processes which may employ conventional vapor-phase fluorination techniques. This includes processes for producing trichlorotrifluoroethane without producing 1,2-dichlorotetrafluoroethane.

SUMMARY OF THE INVENTION

A process is provided in accordance with this invention for producing a reaction product comprising $C_2Cl_3F_3$ substantially free of 1,2-dichlorotetrafluoroethane. The process comprises the steps of (i) contacting a feed mixture consisting essentially of compounds of the formula $C_2Cl_{4-x}F_{2+x}$ (where x is 0 or 1) wherein the $C_2Cl_4F_2$ content is between about 10 mole percent and 90 mole percent of said $C_2Cl_{4-x}F_{2+x}$ and wherein the mole ratio of the total amount of $CCl_2FCCl_2F$ and $CCl_2FCClF_2$ (i.e., the more symmetric $C_2Cl_{4-x}F_{2+x}$ isomers) to the total amount of $CCl_3CClF_2$ and $CCl_3CF_3$ (i.e., the more unsymmetric $C_2Cl_{4-x}F_{2+x}$ isomers) is at least about 1:9, with an isomerization catalyst to produce isomerization product wherein there is less than about 50,000 parts by weight total $CCl_2FCCl_2F$ and $CCl_2FCClF_2$ per million parts by weight total of $CCl_3CClF_2$ and $CCl_3CF_3$; (ii) contacting the isomerization product with HF in the vapor phase in the presence of a fluorination catalyst comprising trivalent chromium at an elevated temperature below 400° C. selected to provide a fluorination product containing $C_2Cl_2F_4$, $C_2Cl_3F_3$ and between about 10 and 90 percent of the $C_2Cl_4F_2$ from the isomerization product, wherein the ratio of $CCl_2FCCl_2F$ to $CCl_3CClF_2$ and the ratio of $CCl_2FCClF_2$ to $CCl_3CF_3$ are both greater than the ratios thereof in the isomerization product and wherein the molar ratio of $CClF_2CClF_2$ to $CCl_2FCClF_2$ is less than about 1:9; (iii) recovering the $C_2Cl_2F_4$ and a first portion of the $C_2Cl_3F_3$ from the fluorination product; and (iv) recycling $C_2Cl_4F_2$ and a second portion of the $C_2Cl_3F_3$ from the fluorination product to step (i) along with an additional amount of $CCl_2FCCl_2F$ which is at least equal to the amount of $C_2Cl_2F_4$ and $C_2Cl_3F_3$ recovered in step (iii) and is sufficient to provide said feed mixture ratio of $C_2Cl_4F_2$ to $C_2Cl_{4-x}F_{2+x}$.

DETAILED DESCRIPTION OF THE INVENTION

Figure 1:
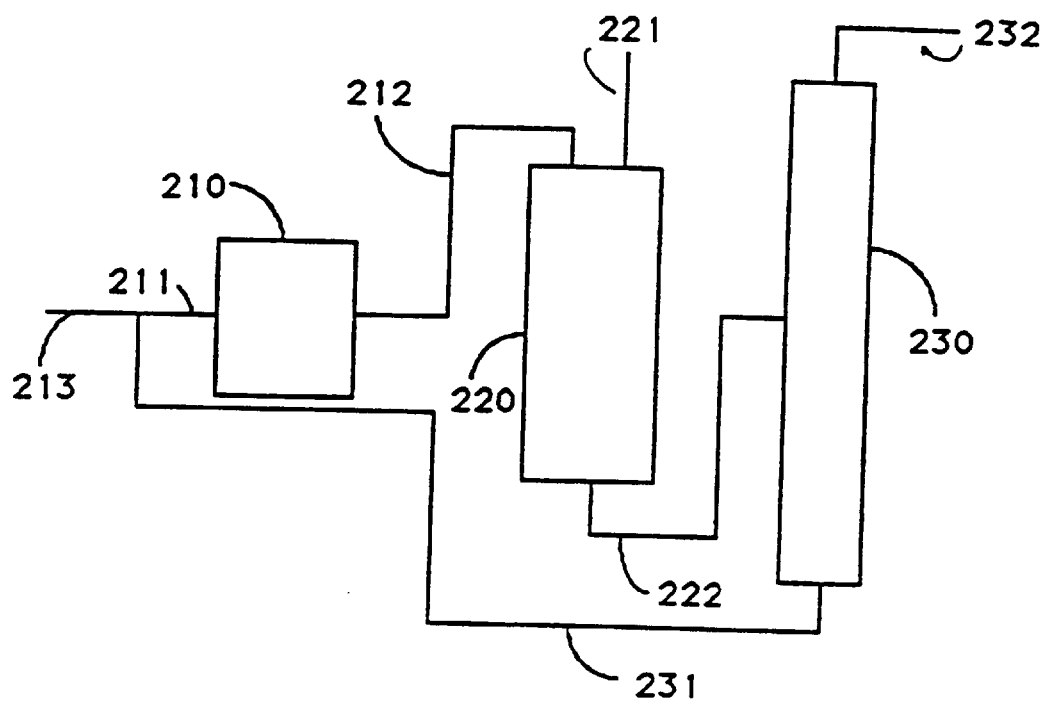
FIG. 1 is a schematic representation of an embodiment of this invention.

The process of this invention involves the vapor-phase catalytic fluorination of a mixture of tetrachlorodifluoroethane isomers. $CCl_2FCClF_2$ reaction product substantially free of $CClF_2CClF_2$ is produced. The $C_2Cl_4F_2$ is present in the mixture of halogenated hydrocarbons used in the fluorination step in a molar ratio of CFC-112 to CFC-112a from about 19:1 to 1:19. Preferably, the ratio of CFC-112 to CFC-112a is less than about 1:1, and more preferably is less than about 1:9. In accordance with this invention, the fluorination is under conditions where there is no substantial production of $CClF_2CClF_2$ (e.g., at an elevated temperature no higher than about 400° C.). No substantial production of $CClF_2CClF_2$ means herein that the molar ratio of $CClF_2CClF_2$ to $CCl_2FCClF_2$ in the fluorination product is less than about 1:9. Preferably, the molar ratio of $CClF_2CClF_2$ to $CCl_2FCClF_2$ in the fluorination product is less than about 1:19, and more preferably is less than about 1:99. The fluorination process according to the present invention can be conducted batchwise, but is preferably conducted continuously in a manner generally known to the art for conducting catalyzed vapor phase fluorination reactions.

The $C_2Cl_4F_2$ mixtures are reacted with hydrogen fluoride using a catalyst comprising trivalent chromium. In addition to a catalytically effective amount of trivalent chromium, such fluorination catalysts can include other components to increase catalyst activity and/or life such as one or more divalent metal ions (e.g., zinc, magnesium, and/or cobalt). The trivalent chromium catalyst may be unsupported (e.g., $Cr_2O_3$) or supported (e.g., on alumina, aluminum fluoride, magnesium fluoride or carbon).

Suitable vapor-phase fluorination catalysts include trivalent chromium halides (e.g., $CrCl_3$ and/or $CrF_3$) supported on carbon. A preferred catalyst is $CrF_3$ on carbon and is disclosed in U.S. Pat. No. 3,632,834, the contents of which are incorporated herein by reference. While any suitable carbon support may be used, a preferred carbon support is acid-washed prior to depositing trivalent chromium on it. Suitable trivalent chromium catalysts may be prepared by treating the carbon used as catalyst support with an acid, preferably with two acids. Typically the support is washed with deionized water after acid treatment and dried; and the chromium halide is then deposited thereon using deposit techniques well known in the art (see e.g., Example 1 of U.S. Pat. No. 3,632,834). Preferably, the chromium content (expressed as $CrCl_3$) is from about 5 to 50 weight percent of the carbon-supported catalyst.

Acid treatment typically uses an acid other than hydrofluoric acid. Preferred acids used for the acid treatment contain neither phosphorus nor sulfur. Examples of acids which may be used in the first acid wash during the catalyst preparation process include organic acids such as acetic acid and inorganic acids, such as HCl or $HNO_3$. Preferably hydrochloric acid or nitric acid is used. The second acid treatment, when employed, advantageously uses hydrofluoric acid. Normally, the carbon is treated with acid such that after such treatment the carbon contains less than about 0.1% by weight ash.

Commercially available carbons which may be treated with acids to provide suitable supports include those sold under the following trademarks: Darco™, Nuchar™, Columbia SBV™, Columbia MBV™, Columbia MBQ™, Columbia JXC™, Columbia CXC™, Calgon PCB™, Norit™ and Barnaby Cheny NB™. The carbon support can be in the form of powder, granules, extrudates, or pellets, etc.

The acid treatment may be accomplished in several ways. A suitable procedure is as follows. A carbon support is soaked overnight with gentle stirring in a 1 molar solution of the acid prepared in deionized water. The carbon support is then separated and washed with deionized water until the pH of the washings is about 3. Preferably, the carbon support is then soaked again with gentle stirring in a 1 molar solution of the acid prepared in deionized water for 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C. The washed carbon is then soaked, if necessary, in 1 molar HF prepared in deionized water for about 48 hours at room temperature with occasional stirring. The carbon support is separated and washed repeatedly with deionized water until the pH of the washings is greater than 4. The carbon support is then dried followed by calcination at about 300° C. for about 3 hours in air prior to its use as a support. Reference is made to U.S. Pat. No. 5,136,113 for further details relating to producing acid-washed carbon catalysts.

For continous processes, the fluorination is generally conducted in the reaction zone for the fluorination. The reaction zone may contain more than one reactor, multiple feed lines, as well as interstage cooling or heating, addition of reactants, diluents, recycle streams, etc. For example, multiple reactors may be used to stage the degree of fluorination so that undue temperature rise and overfluorination are avoided. The reaction product is normally recovered at the end of the reaction zone. If necessary, the reaction products, intermediates and/or by-products can be removed at various stages of the reaction zone and if desired recycled to different parts of the reaction zone. For example, HF and $C_2Cl_4F_2$ can be fed to a reaction zone at more than one feed location. $CCl_2FCClF_2$ (CFC-113), is generally recovered from the end of the reaction zone.

Suitable fluorination reaction temperatures are normally from about 250° C. to 400° C. A preferred temperature range is from 275° C. to 375° C., with temperatures ranging from 300° C. to 350° C. being particularly preferred. The HF to $C_2Cl_4F_2$ ratio is normally from 0.2:1 to 4:1, and preferably ranges from 0.25:1 to 2:1. Pressure is not critical. Atmospheric and superatmospheric pressures (e.g., from about 100 kPa to about 7000 kPa) are the most convenient and are therefore preferred. The above reaction variables together with the catalyst loading are balanced one against the other such that in the fluorination products there is a molar ratio of $CClF_2CClF_2$ to $CCl_2FCClF_2$ in the product mixture which is less than about 1:9. One skilled in the art will recognize that higher temperatures and higher $HF:C_2Cl_4F_2$ ratios favor a higher degree of fluorination. The amount of overfluorination can thus be reduced by providing a lower $HF:C_2Cl_4F_2$ ratio and/or lower temperature. Catalyst contact time can also be adjusted in a conventional manner to control fluorination.

The product mixture from fluorination normally contains a mixture of $C_2Cl_3F_3$ (almost exclusively $CCl_2FCClF_2$) small amounts of $CClF_2CF_3$ (CFC-115), $CClF_2CClF_2$, $CCl_2FCF_3$ (CFC-114a), unreacted $C_2Cl_4F_2$ isomers and HF and HCl. The fluorination product is separated such that a portion of the $C_2Cl_3F_3$ (and any $C_2Cl_2F_4$) in the product mixture is separated from $C_2Cl_4F_2$ therein. Typically, conventional separation using one or more distillation column (s) is employed. The separation may also include one or more decanter(s). During separation by distillation, the lower boiling materials (e.g., HF, HCl, CFC-115) are separated from the CFC-112 isomers. It is noted that azeotropes of HF with various halocarbons such as $CCl_2FCCl_2F$, $CCl_3CClF_2$, $CCl_3CF_3$, and $CCl_2FCF_3$ can form during distillation.

The CFC-112 isomers from the fluorination product (which are normally enriched in CFC-112 as a result of selective fluorination of CFC-112a) and a portion of the CFC-113 isomer from the fluorination product are fed along with additional CFC-112 to an isomerization zone, where the CFC-112 is substantially converted to CFC-112a. HF should be removed from the $C_2Cl_4F_2$ prior to contact with the isomerization catalyst. The $C_2Cl_3F_3$ present in the mixture of $C_2Cl_3F_3$ and $C_2Cl_4F_2$ fed to the isomerizer provides a melting point below the melting point of $CCl_2FCCl_2F$, thereby facilitating the desired isomerization. Preferably, the $C_2Cl_4F_2$ content is between about 10 mole percent and 75 mole percent of the $C_2Cl_{4-x}F_{2+x}$ fed to the isomerization step; and more preferably the $C_2Cl_4F_2$ content is between about 10 mole percent and 50 mole percent thereof. The CFC-112 is isomerized to CFC-112a in the presence of recycled $C_2Cl_3F_3$ using an aluminum chloride catalyst as disclosed in Example IV of U.S. Pat. No. 2,598,411. Isomerization of recycled $CCl_2FCClF_2$ may be accomplished in the same isomerization reactor as used for the isomerization of CFC-112 to CFC-112a. However, in accordance with this invention, the molar ratio of $C_2Cl_4F_2$ to $C_2Cl_3F_3$ fed to the isomerization zone is at least about 1:9. The molar ratio of $(CCl_2FCClF_2+CCl_2FCCl_2F)$ to $(CCl_3CF_3+CCl_3CClF_2)$ in the compounds fed to the isomerization generally at least about 1:9. Many aluminum trihalide catalysts can be employed. A preferred catalyst is an anhydrous aluminum trichloride which has been micropulverized (i.e., mechanically comminuted by crushing, ball milling, rod milling, grinding or the like) to provide a surface area of greater than about 0.8 $m^2/g$ and has been activated by treatment under agitation with at least about 10 g $CCl_2FCClF_2$ per gram of aluminum trichloride. Reference is made to copending U.S. patent application Ser. No. 08/117,379 for further disclosure of micropulverized catalysts. The CFC-112a is recycled in accordance with this invention to the fluorination step.

The CFC-113 recovered from the separation zone also may be isomerized to CFC-113a using the aluminum chloride catalyst as disclosed in Example I of U.S. Pat. No. 2,598,411. As above, preferred catalysts include an activated micropulverized anhydrous aluminum trichloride with a surface area of greater than about 0.8 $m^2/g$.

The CFC-113a from the isomerization zone can readily be reacted with HF in a reaction zone to afford high purity CFC-114a. The latter compound can then be converted by hydrogenolysis to $CH_2FCF_3$ (HFC-134a), a non-ozone depleting refrigerant.

Employment of the instant invention is further illustrated by reference to FIG. 1 wherein a mixture of $C_2Cl_4F_2$ isomers containing substantial CFC-112 and optionally $C_2Cl_3F_3$ isomers containing substantial CFC-113 (i.e., the ratio of CFF-113 to CFC-113a is greater than 100:1) is fed through line (211) to an isomerizer (210). The isomerizer effluent consisting of a mixture of $C_2Cl_4F_2$ isomers containing predominantly CFC-112a and optionally $C_2Cl_3F_3$ isomers containing predominantly CFC-113a is fed through line (212) to a fluorination reactor (220). HF is fed to reactor (220) through line (221). The fluorination reactor effluent containing unreacted $CCl_2FCClF_2$, unreacted $C_2Cl_4F_2$, HF and HCl and optionally $C_2Cl_2F_4$ isomers containing predominantly $CCl_2FCF_3$ is fed through line (222) to a distillation column (230). A mixture of $C_2Cl_3F_3$ isomers, HF and HCl and optionally $C_2Cl_2F_4$ isomers is collected at the top of the column and recovered through line (232). A mixture of $C_2Cl_4F_2$ isomers enriched in CFC-112 and $C_2Cl_3F_3$ enriched in CFC-113, from the bottom of column (230), is fed through line (231) back to the isomerizer (210) along with additional CFC-112 through line (213).

The reactors and their associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

Practice of the invention will become further apparent from the following non-limiting examples.

EXAMPLES

General Reaction Procedure

A ⅝" (1.58 cm) I.D. Inconel® nickel alloy reactor was charged with a catalyst and heated to 300° C. in a flow of nitrogen (25 mL/min) for about 20 hours. The temperature was reduced to 175° C. and a 2:1 molar ratio of nitrogen and HF was started through the reactor (total flow 100 mL/min). After one hour under these conditions, the molar ratio of nitrogen to HF was adjusted to 1:3 and the temperature increased gradually over a two hour period to 400° C. The reactor was then brought to the desired operating temperature, the nitrogen flow stopped, and the flow of reactants started.

General Analytical Procedure

The reactor effluent was sampled on-line with a Hewlett Packard HP 5890 gas chromatograph using a 20 foot (6.1 m) long, one-eighth inch (0.32 cm) diameter, column containing Krytox™ perfluorinated polyether on an inert support and a helium flow of 35 mL/min. Gas chromatographic conditions were 70° C. for three minutes followed by temperature programming to 180° C. at a rate of 6° C./minute. The table percentages are in mole %.

EXAMPLE 1

Fluorination of $CCl_2FCCl_2F/CCl_2FCClF_2$ Mixtures

The General Reaction Procedure was followed using a 29% $CrCl_3$ on carbon catalyst (10.8 g, 25 mL), a molar composition of chlorofluorocarbons (CFCs) containing $CCl_2FCCl_2F$ (64.7%), $CCl_2FCClF_2$ (35.1%), and $CCl_3CF_3$ (0.2%), an HF:CFCs molar ratio of 2:1 and a contact time of 30 seconds. The reaction was run at atmospheric pressure.

The results at various temperatures are shown in Table 1.

TABLE 1

| Temp. (°C.) | 115[a] | 114[b] | 114a[c] | 113[d] | 113a[e] | 112/a[f] |
|---|---|---|---|---|---|---|
| 325 | 0.2 | 1.6 | 1.3 | 55.1 | 0.2 | 41.0 |
| 350 | 0.4 | 4.6 | 1.9 | 69.3 | 0.3 | 22.7 |
| 375 | 0.9 | 9.7 | 3.6 | 73.7 | 0.4 | 10.3 |

[a]115 is $CClF_2CF_3$
[b]114 is $CClF_2CClF_2$
[c]114a is $CCl_2FCF_3$
[d]113 is $CCl_2FCClF_2$
[e]113a is $CCl_3CF_3$
[f]112/a is $CCl_2FCCl_2F + CCl_3CClF_2$ (The isomers of $C_2Cl_4F_2$ cannot be distinguished using the above analytical method. In this example it is believed that the product consists essentially of $CCl_2FCCl_2F$).

Other products identified include $CF_3CF_3$, $CCl_2$=CClF, $CCl_3CCl_2F$ and $CCl_2$=$CCl_2$.

EXAMPLE 2

Fluorination of $CCl_3CClF_2/CCl_2FCClF_2$ Mixtures

The General Reaction Procedure was followed using a 29% $CrCl_3$ on carbon catalyst (10.8 g, 25 mL), a molar composition of chlorofluorocarbons (CFCs) containing $CCl_3CClF_2$ (63.8%), $CCl_2FCClF_2$ (35.8%), and $CCl_3CF_3$ (0.2%), an HF:CFCs molar ratio of 2:1 and a contact time of 30 seconds. The reaction-was run at atmospheric pressure. The results at various temeperatures are shown in Table 2.

TABLE 2

| Temp. (°C.) | 115 | 114 | 114a | 113 | 113a | 112/a[a] |
|---|---|---|---|---|---|---|
| 300 | 0.1 | 0.9 | 0.7 | 90.9 | 0.5 | 6.2 |
| 325 | 0.1 | 3.2 | 1.6 | 90.1 | 0.4 | 3.9 |
| 350 | 0.3 | 6.0 | 2.1 | 86.9 | 0.4 | 3.9 |

112/a is $CCl_2FCCl_2F + CCl_3CClF_2$ (The isomers of $C_2Cl_4F_2$ cannot be distinguished using the above analytical method. In this example it is believed that the product consisted essentially of $CCl_3CClF_2$).

Other products identified include $CCl_2$=CClF and $CCl_2$=$CCl_2$.

Particular embodiments of the invention are illustrated in the Examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims which follow.

I claim:

1. A process for producing a reaction product comprising $C_2Cl_3F_3$ substantially free of $CClF_2CClF_2$, comprising the steps of:
   (i) contacting a feed mixture consisting essentially of compounds of the formula $C_2Cl_{4-x}F_{2+x}$ wherein x is 0 or 1 wherein the $C_2Cl_4F_2$ content is between about 10 mole percent and 90 mole percent of said $C_2Cl_{4-x}F_{2+x}$ and wherein the mole ratio of the total amount of $CCl_2FCCl_2F$ and $CCl_2FCClF_2$ to the total amount of $CCl_3CClF_2$ and $CCl_3CF_3$ is at least about 1:9, with an isomerization catalyst to produce isomerization product wherein there is less than about 50,000 parts by weight total $CCl_2FCCl_2F$ and $CCl_2FCClF_2$ per million parts by weight total of $CCl_3CClF_2$ and $CCl_3CF_3$;

(ii) contacting the isomerization product with HF in the vapor phase in the presence of a fluorination catalyst comprising trivalent chromium at an elevated temperature below 400° C. selected to provide a fluorination product containing $C_2Cl_2F_4$, $C_2Cl_3F_3$ and between about 10 and 90 percent of the $C_2Cl_4F_2$ from the isomerization product, wherein the ratio of $CCl_2FCCl_2F$ to $CCl_3CClF_2$ and the ratio of $CCl_2FCClF_2$ to $CCl_3CF_2$ are both greater than the ratios thereof in the isomerization product and wherein the molar ratio of $CClF_2CClF_2$ to $CCl_2FCClF_2$ is less than about 1:9;

(iii) recovering the $C_2Cl_2F_4$ and a first portion of the $C_2Cl_3F_3$ from the fluorination product; and (iv) recycling $C_2Cl_4F_2$ and a second portion of the $C_2Cl_3F_3$ from the fluorination product to step (i) along with an additional amount of $CCl_2FCCl_2F$ which is at least equal to the amount of $C_2Cl_2F_4$ and $C_2Cl_3F_3$ recovered in step (iii) and is sufficient to provide said feed mixture ratio of $C_2Cl_4F_2$ to $C_2Cl_{4-x}F_{2+x}$.

2. The process of claim 1 wherein the fluorination catalyst comprises trivalent chromium supported on acid-washed carbon.

3. The process of claim 2 wherein the fluorination catalyst is a chromium halide supported on acid-washed carbon.

4. The process of claim 3 wherein the chromium content of the catalyst is from 5 to 50 weight percent expressed as $CrCl_3$.

5. The process of claim 1 wherein the $C_2Cl_4F_2$ content of the feed mixture is between about 10 mole percent and 75 mole percent of the $C_2Cl_{4-x}F_{2+x}$ therein.

6. The process of claim 1 wherein the $C_2Cl_4F_2$ content of the feed mixture is between about 10 mole percent and 50 mole percent of the $C_2Cl_{4-x}F_{2+x}$ therein.

7. The process of claim 1 wherein the fluorination reaction temperature is from about 250° C. to 350° C.

8. The process of claim 1 wherein the $HF:C_2Cl_4F_2$ ratio for the fluorination step is from 0.2:1 to 4:1.

9. The process of claim 1 wherein the molar ratio of $CClF_2CClF_2$ to $CCl_2FCClF_2$ in the fluorination product is less than about 1:19.

10. The process of claim 1 wherein the molar ratio of $CClF_2CClF_2$ to $CCl_2FCClF_2$ in the fluorination product is less than about 1:99.

* * * * *